(12) United States Patent
Baxter

(10) Patent No.: US 6,648,898 B1
(45) Date of Patent: Nov. 18, 2003

(54) CLIP APPLYING APPARATUSES AND METHODS FOR VASCULAR LIGATION

(75) Inventor: Jeffrey Wayne Baxter, San Jose, CA (US)

(73) Assignee: CardioThoracic Systems, Inc., Santa Clara, CA (US)

( * ) Notice: Subject to any disclaimer, the term of this patent is extended or adjusted under 35 U.S.C. 154(b) by 0 days.

(21) Appl. No.: 09/517,762

(22) Filed: Mar. 2, 2000

(51) Int. Cl.[7] ............................................... A61B 17/04
(52) U.S. Cl. ....................................................... 606/142
(58) Field of Search ................................. 606/142, 143

(56) References Cited

U.S. PATENT DOCUMENTS

| | | | | |
|---|---|---|---|---|
| 4,763,669 A | * | 8/1988 | Jaeger | 128/751 |
| 5,192,288 A | * | 3/1993 | Thompson et al. | 606/143 |
| 5,395,381 A | * | 3/1995 | Green et al. | 606/143 |
| 5,403,327 A | * | 4/1995 | Thornton et al. | 606/143 |
| 5,749,881 A | * | 5/1998 | Sackier et al. | 606/151 |
| 6,270,508 B1 | * | 8/2001 | Klieman et al. | 606/147 |

\* cited by examiner

Primary Examiner—Gary Jackson
(74) Attorney, Agent, or Firm—Blakely, Sokoloff, Taylor & Zafman LLP

(57) ABSTRACT

An apparatus and method for applying ligating clips to perform minimally invasive vascular ligation. An actuating assembly contacts a clip applier to actuate the clip applier among at least a first position, a second position and a third position. The clip applier is capable of receiving a first ligating clip when the clip applier is in the first position and a second ligating clip when the clip applier is in the second position. The actuating assembly actuates the clip applier to the third position to close the ligating clip being held by the clip applier.

12 Claims, 9 Drawing Sheets

US 6,648,898 B1

CLIP APPLYING APPARATUSES AND METHODS FOR VASCULAR LIGATION

BACKGROUND OF THE INVENTION

1. Field of the Invention

The present invention relates generally to vascular ligation, and more specifically to clip appliers for vascular ligation.

2. Background Information

Vascular ligation is an important component of a number of surgical procedures. For example, vascular ligation is part of the process of endoscopic vessel harvesting, such as harvesting of the saphenous vein to perform a coronary bypass procedure. Vascular ligation is also an integral part of vein harvesting performed in situ or during a femoral popliteal bypass procedure. Specifically, the tributaries of the saphenous vein must be ligated before the harvesting of the vein can actually occur. Common techniques for performing vascular ligation involve the use of ligating clips and clip appliers. However, current clip appliers are often suited for only open surgery. In addition, ligating clips are often formed in different sizes such that vessels of varying dimensions can be ligated.

Vein harvesting is typically a traumatic procedure, and the common techniques for positioning and applying ligating clips can contribute to the invasiveness of the vein harvesting procedure. Increased trauma to the patient's body can be dangerous and often leads to a longer recovery period for the patient. Thus, being able to position and apply ligating clips in a minimally invasive manner is desirable because of the need to limit the trauma to a patient's body.

SUMMARY OF THE INVENTION

The present invention provides in one embodiment a clip applier in contact with an actuating assembly which actuates the clip applier among at least a first position, a second position and a third position. The clip applier can receive a first ligating clip when the clip applier is in the first position, and the clip applier can receive a second ligating clip when the clip applier is in the second position.

In one embodiment of the present invention, the clip applier includes a jaw having first and second movable sections adjacent to each other. In another embodiment, the first section is rotatably coupled to the second section, which is translatably actuated by the actuating assembly. In yet another embodiment, the first and second movable sections are resilient and are urged together by the actuating assembly.

Additional features and benefits of the present invention will become apparent from the detailed description, figures and claims set forth below.

BRIEF DESCRIPTION OF THE DRAWINGS

Various embodiments of the present invention will be described in detail with reference to the following drawings in which like reference numerals refer to like elements. The present invention is illustrated by way of example and not limitation in the accompanying figures.

DETAILED DESCRIPTION

The following description provides embodiments of the present invention. However, it will be appreciated that other embodiments of the present invention will become apparent to those of ordinary skill in the art upon examination of this description. Thus, the present description and accompanying drawings are for purposes of illustration and are not to be used to construe the invention in a restrictive manner.

The present invention provides a clip applier that is in actuatable contact with an actuating assembly that actuates the clip applier among a variety of positions. Because the clip applier can be positioned variously, it is capable of holding one at a time ligating clips of different sizes and applying them to the target vessel. The clip applier includes a jaw having first and second movable sections adjacent to each other. In one embodiment of the present invention, the first movable section is rotatably coupled to the second movable section, which is translatably actuated by the actuating assembly. The movement, and hence position, of the first movable section is dictated by the movement of the second movable section. In another embodiment of the present invention, the first and second movable sections are resilient and are urged by the actuating assembly to different positions.

Figure 1A:
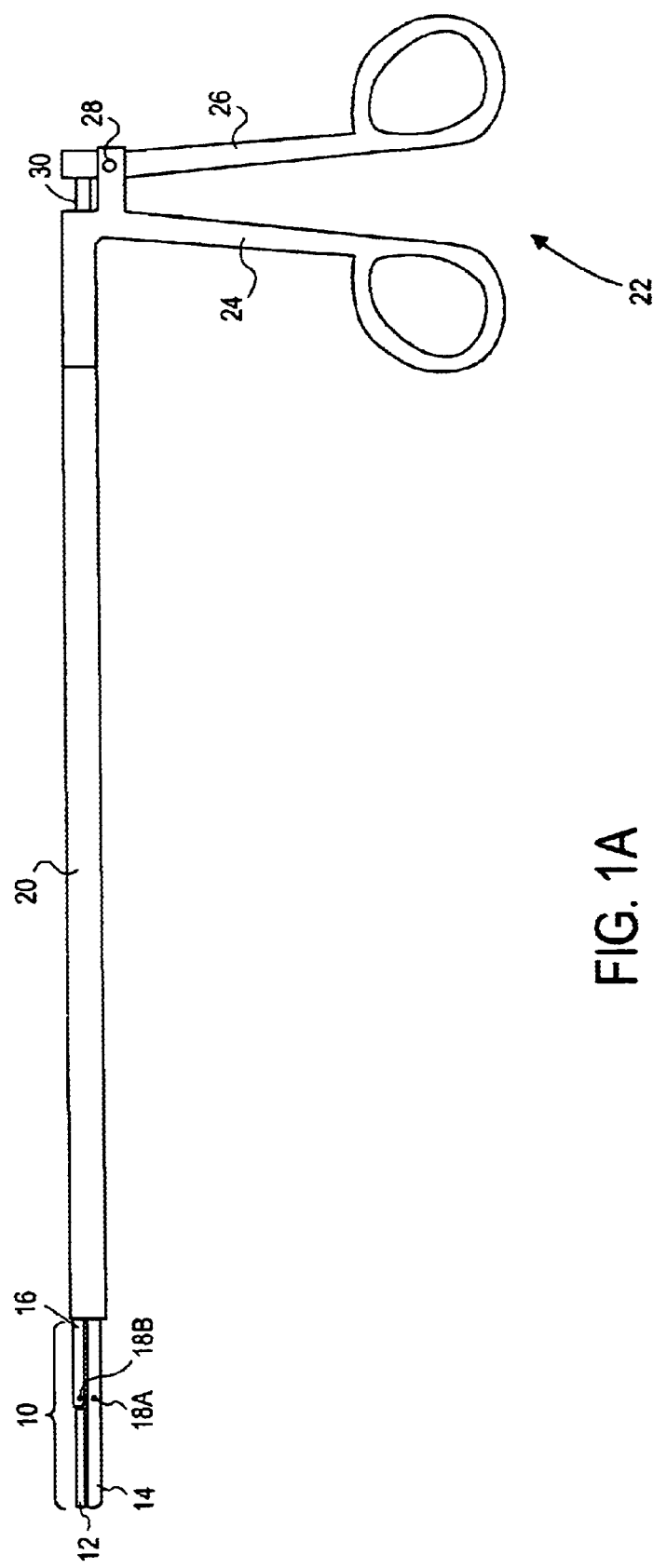
FIG. 1A shows a side view of one embodiment of a clip applier and actuating assembly in accordance with the teachings of the present invention.
Figure 1B:
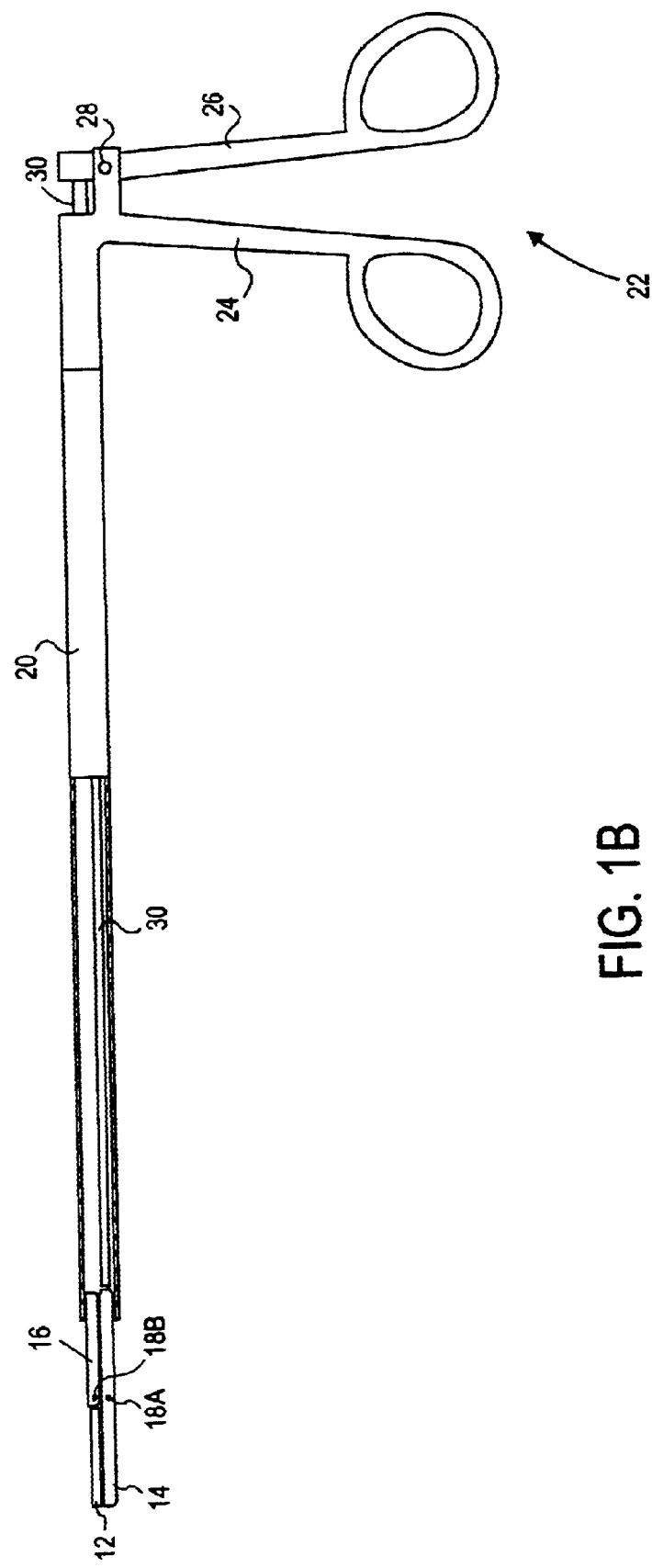
FIG. 1B shows a partial cutaway view of the clip applier and actuating assembly shown in FIG. 1A.

FIGS. 1A and 1B show a side view and a partial cutaway view, respectively, of one embodiment of a clip applier and actuating assembly according to the present invention. A clip applier 10 includes a fixed support member 16 and a jaw having a rotating section 12 and a translating section 14. Section 12 is rotatably coupled to section 14 by a pin 18*a*. Section 12 is also rotatably coupled to member 16 by a pin 18*b*. Member 16 is fixed to the inner surface of a housing 20 via any suitable means such as, for example, a screw or an adhesive. Member 16 could also be integrally formed with and extending from an end of housing 20. Housing 20 is an elongated, rigid or flexible shaft which is coupled to a handle 22. It is appreciated that housing 20 can be integrally formed with handle 22.

Handle 22 is in a scissors-like form and includes a stationary member 24 and an actuating member 26 which is rotatably coupled to stationary member 24 via a pin 28. An actuating rod 30 is attached to, or integrally formed with, actuating member 26. Rod 30 extends through housing 20 and is coupled to an end of translating section 14. In one embodiment, rod 30 is coupled to section 14 in any suitable manner such that rod 30 can push and pull section 14 in a translating fashion. Housing 20 not only houses actuating rod 30 but also acts as an anchor for fixed support member 16. Housing 20 and rod 30 can be flexible to provide greater accessibility to target vessels, but it should be noted that rod 30 is also rigid enough to provide a pushing force to section 14. It is appreciated that housing 20 and rod 30 can be formed in various lengths depending on the expected distance between the target vessels and the insertion point on the patient's body. Furthermore, the cross sectional shape of housing 20 can be a variety of shapes including circular.

Sections 12 and 14 and member 16 can be made of surgical steel, stainless steel, plastic or similar materials. Rod 30 can also be made of surgical steel or a similar material. Housing 20 can be made of plastic, stainless steel or other appropriate materials.

Because sections 12 and 14 can be actuated remotely via rod 30, and clip applier 10 and housing 20 are elongated with a thin profile, the present invention can be used minimally invasively to perform vascular ligation. This will help prevent the vascular ligation procedure from exacerbating the invasiveness associated with vein harvesting procedures.

Figure 2B:
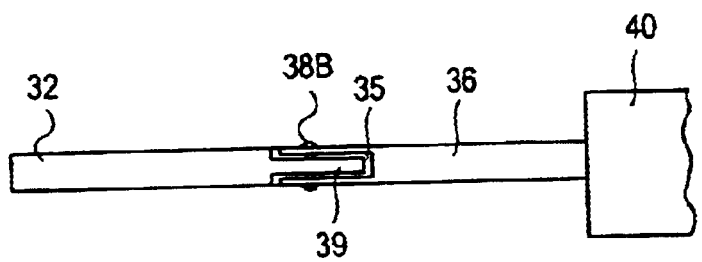
FIGS. 2A–2C show side, top and bottom views, respectively, of a clip applier in accordance with the teachings of the present invention.
Figure 2A:
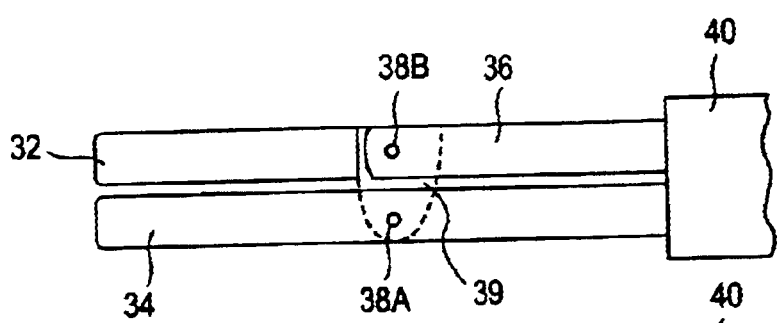
Figure 2C:
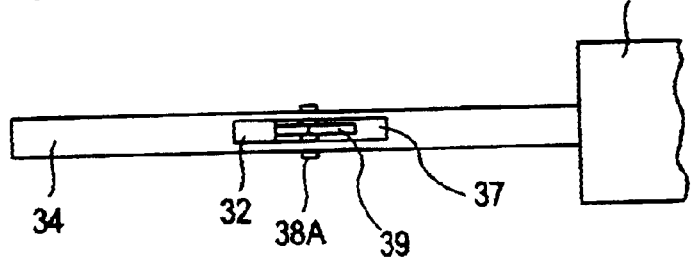

FIGS. 2A–2C show side, top and bottom views, respectively of a clip applier similar to the one shown in FIGS. 1A and 1B. The clip applier includes a fixed support member 36 and a jaw having a rotating section 32 and a translating section 34. A flange 39 extending from section 32 is rotatably coupled to section 34 by a pin 38a. Flange 39 extending from section 32 is also rotatably coupled to member 36 by a pin 38b. A gap 35 in member 36 accommodates flange 39. A gap 37 in section 34 also accommodates flange 39. Gaps 35 and 37 are large enough to allow flange 39, and hence section 32, to be rotated. Member 36 is attached to housing 40 as described above in conjunction with member 16 and housing 20. Member 36 is shown extending from within housing 40, but it is appreciated that member 36 can be integrally formed with housing 40 such that member 36 extends from an end of housing 40.

Figure 3A:
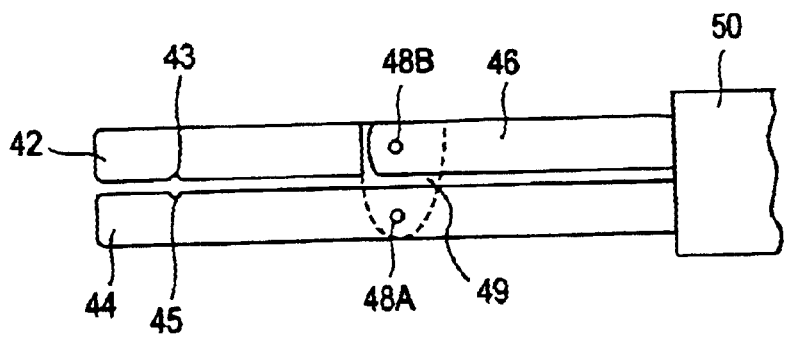
FIGS. 3A–3C show varying positions of a clip applier in accordance with the teachings of the present invention.
Figure 3B:
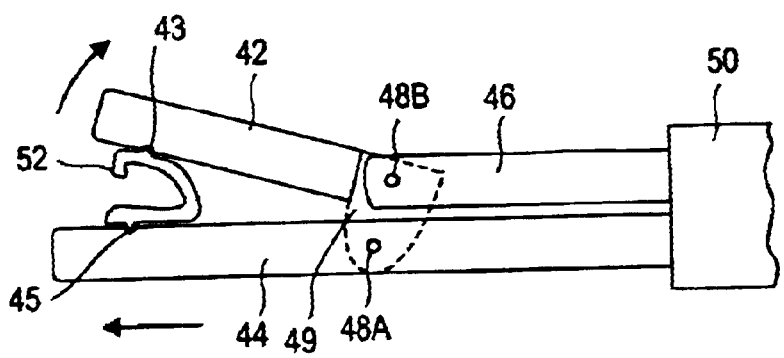
Figure 3C:
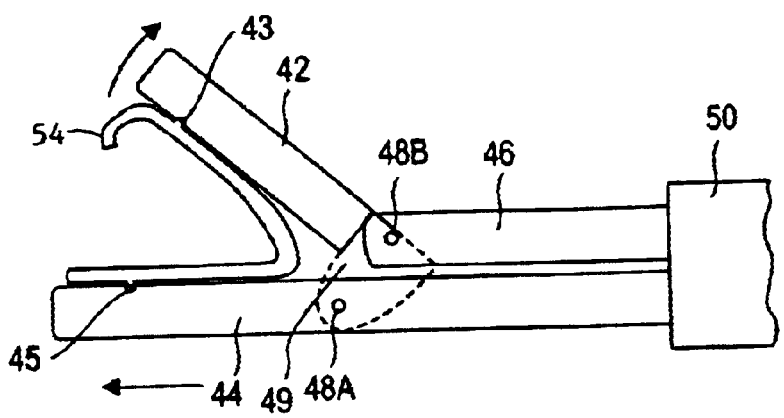

FIGS. 3A–3C show varying positions of a clip applier according to the present invention. FIG. 3A shows a clip applier in a closed position. The clip applier includes a fixed support member 46 and a jaw having a rotating section 42 and a translating section 44. Sections 42 and 44 are formed with notches 43 and 45, respectively. A flange 49 extending from rotating section 42 is rotatably coupled to section 44 by a pin 48a. Flange 49 is also rotatably coupled to member 46 by a pin 48b. Member 46 is attached to housing 50 as described above with respect to similar embodiments.

FIG. 3B shows the clip applier in a slightly open position. As translating section 44 translates away from housing 50, rotating section 42 rotates away from section 44 due to the movement of section 44 and the coupling of flange 49 to section 44 and member 46 via pins 48a and 48b, respectively, to create an opening between sections 42 and 44. This opening can receive a ligating clip 52, which is held securely by the mating of protrusions on clip 52 with notches 43 and 45. An example of such a ligating clip with protrusions is the ABSOLOK line of ligating clips by Ethicon, Inc. If the ligating clip does not have protrusions or notches 43 and 45 are otherwise unnecessary, it is appreciated that the surfaces of sections 42 and 44 can be textured to provide a better mechanical or friction fit between the clip and sections 42 and 44.

FIG. 3C shows the clip applier in a more pronounced open position. As translating section 44 translates farther away from housing 50, rotating section 42 rotates farther away from section 44 to enlarge the opening between sections 42 and 44. Because of the increased space in the opening between sections 42 and 44, a larger ligating clip 54 can be held in the opening between sections 42 and 44. Thus, in accordance with the teachings of the present invention, the jaw of the clip applier can be actuated to different positions to accommodate ligating clips of different sizes.

Figure 4A:
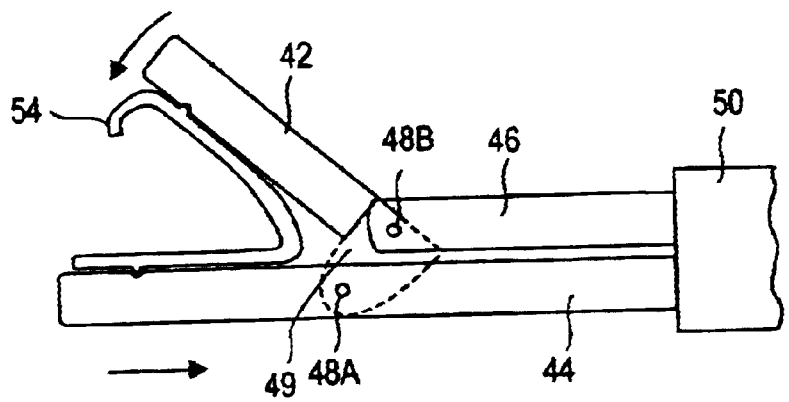
FIGS. 4A–4C show a clip applier engaging a ligating clip in successive positions in accordance with the teachings of the present invention.
Figure 4B:
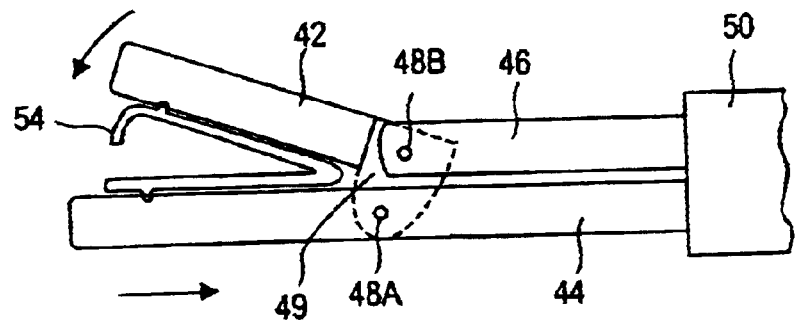
Figure 4C:
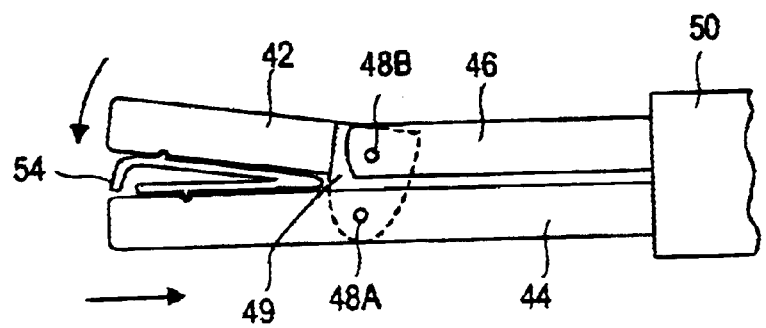

FIGS. 4A–4C show the clip applier shown in FIG. 3C engaging ligating clip 54 in successive positions to close ligating clip 54. As translating section 44 moves toward housing 50, rotating section 42 rotates toward section 44 due to the movement of section 44 and the coupling of flange 49 to section 44 and member 46 via pins 48a and 48b, respectively. As section 42 rotates toward section 44, section 42 applies a force to the contacted portion of clip 54 to gradually close clip 54. Assuming clip 54 is positioned around the target vessel (not shown) while clip 54 is open, clip 54 will be clamped over the target vessel when it is closed. Once clip 54 is deployed, rotating section 42 can be opened according to the above description to allow the clip applier to be disengaged from clip 54. Once the clip applier is removed from the patient's body, the clip applier can be engaged with another ligating clip of the same or different size.

It is appreciated that the shape and configuration of the jaw sections typically depends on factors such as the size and shape of the ligating clips to be used and the desired secureness with which the clips are held during the transit and application of the clips. Thus, the shape and configuration of the jaw sections shown in the figures are to be understood as examples of the present invention.

Figure 5A:
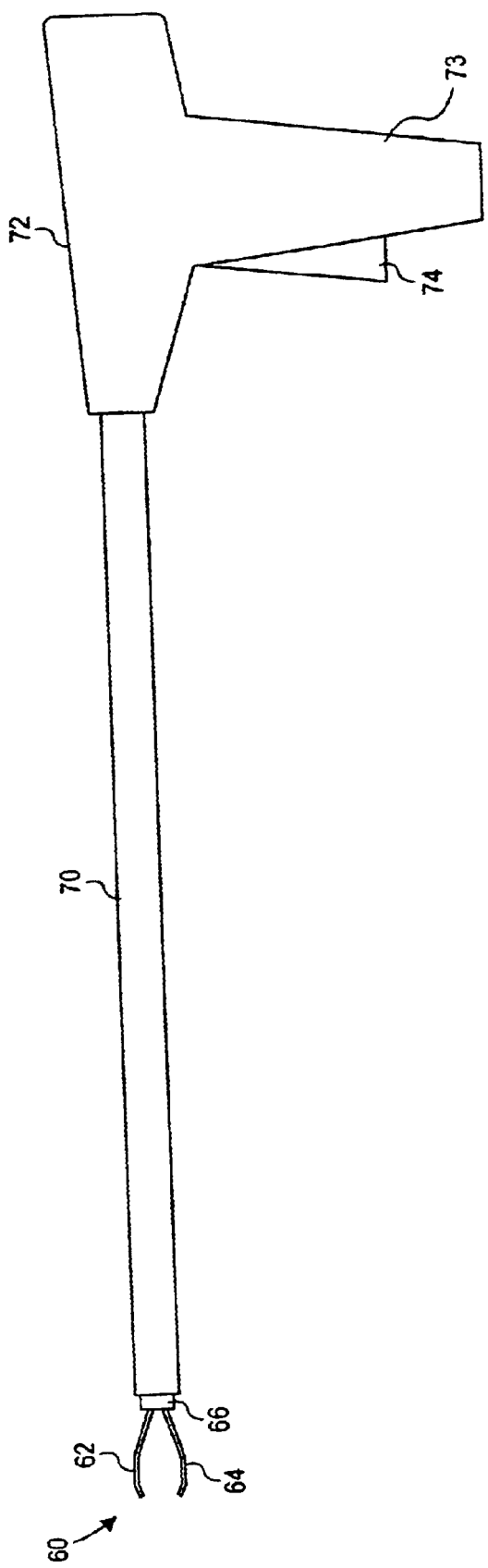
FIG. 5A shows a side view of another embodiment of a clip applier and actuating assembly in accordance with the teachings of the present invention.
Figure 5B:
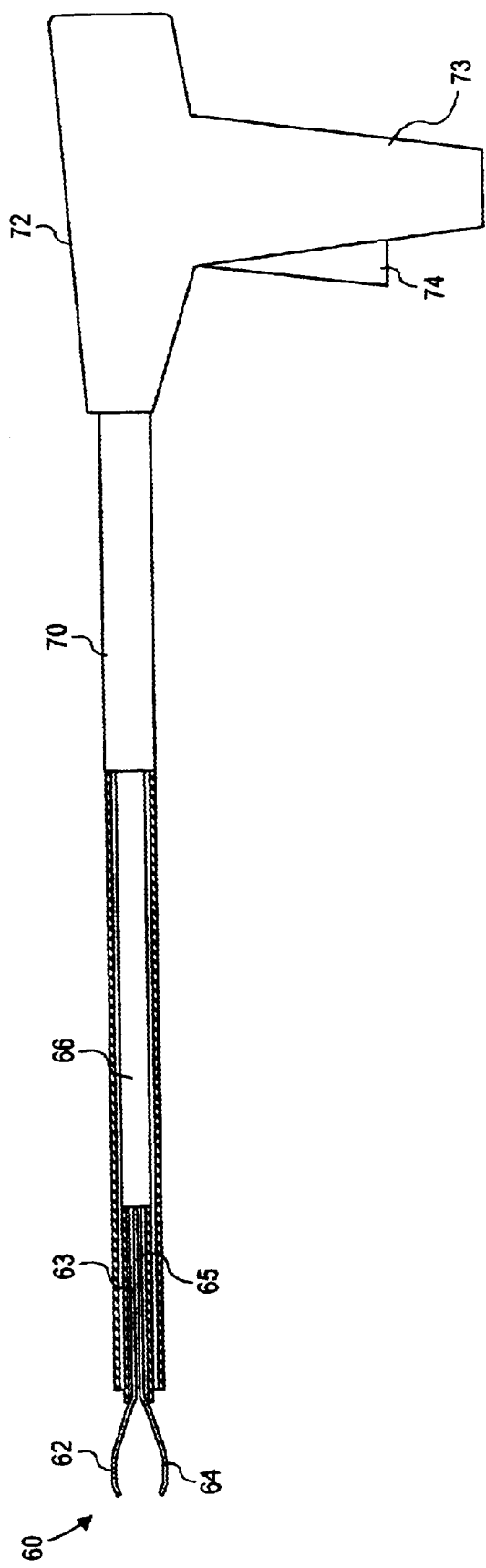
FIG. 5B shows a partial cutaway view of the clip applier and actuating assembly shown in FIG. 5A.

FIGS. 5A and 5B show a side view and a partial cutaway view, respectively, of another embodiment of a clip applier and actuating assembly according to the present invention. A clip applier 60 includes a jaw having a first resilient section 62 and a second resilient section 64. Sections 62 and 64 have stems 63 and 65, respectively, that are housed within an actuating housing 66, which is translatably housed within a main housing 70. Sections 62 and 64 and stems 63 and 65 can be made of surgical steel, stainless steel or similar materials. Actuating housing 66 can also be made of surgical steel or a similar material. Main housing 70 can be made of plastic, stainless steel or other appropriate materials. Sections 62 and 64 extend out from actuating housing 66, which is typically in the shape of an elongated tube. Main housing 70 is also typically in the shape of an elongated tube such that main housing 70 and actuating housing 66 are in a substantially concentric relationship. It is appreciated that main housing 70 and actuating housing 66 need not be tubular. Main housing 70 and actuating housing 66 can be shaped variously to allow actuating housing 66 to move within main housing 70. Furthermore, main housing 70 and actuating housing 66 can be slightly flexible to provide greater accessibility to target vessels.

Main housing 70 is coupled to a handle base 72 having a handle 73 and a trigger 74 extending from within handle 73. Alternatively, main housing 70 is integrally formed with handle base 72. Trigger 74 can be part of any conventional trigger mechanism located within handle 73 and handle base 72 such that when trigger 74 is depressed, actuating housing 66 translates away from handle base 72, and when trigger 74 is released, actuating housing 66 translates toward handle base 72. The trigger mechanism has not been shown so as not to obscure the present invention. It should be noted that stems 63 and 65 are typically anchored within main housing 70 or handle base 72 such that resilient sections 62 and 64 do not move back and forth as actuating housing 66 moves back and forth.

Because sections 62 and 64 can be actuated remotely via actuating housing 66, and clip applier 60 and housing 70 are elongated with a thin profile, the present invention can be used minimally invasively to perform vascular ligation. This will help prevent the vascular ligation procedure from exacerbating the invasiveness associated with vein harvesting procedures.

Figure 6A:
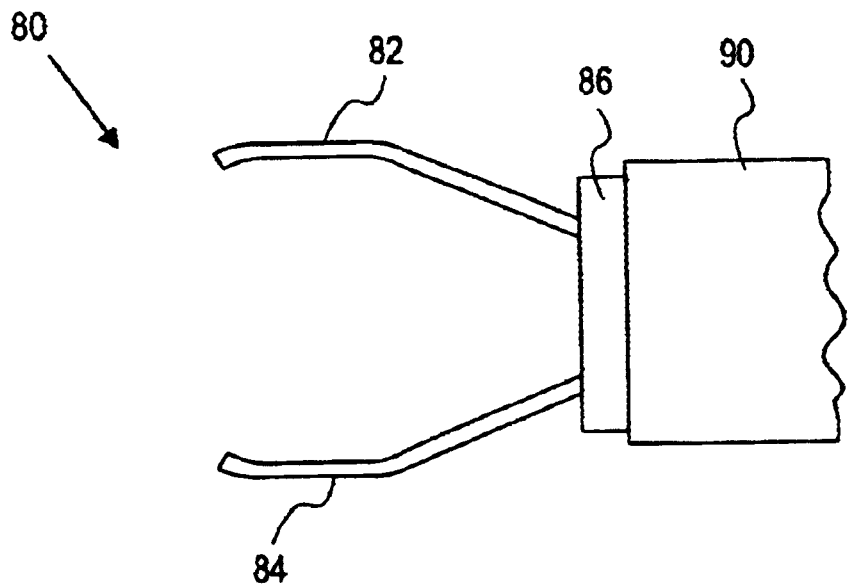
FIGS. 6A and 6B show side and top views, respectively, of a clip applier in accordance with the teachings of the present invention.
Figure 6B:
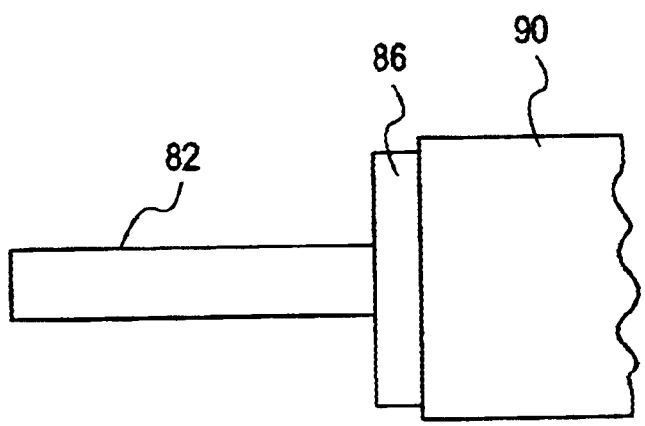

FIGS. 6A and 6B show side and top views, respectively, of a clip applier 80 similar to the one shown in FIGS. 5A and 5B. Clip applier 80 includes a jaw having a first resilient section 82 and a second resilient section 84. Sections 82 and 84 have stems (not shown) similar to stems 63 and 65 that are housed within an actuating housing 86, which is translatably housed within a main housing 90. The angle and shape of sections 82 and 84 can be varied depending on factors such as the size and shape of the ligating clips to be used and the desired secureness with which the clips are held during the transit and application of the clips.

Figure 7A:
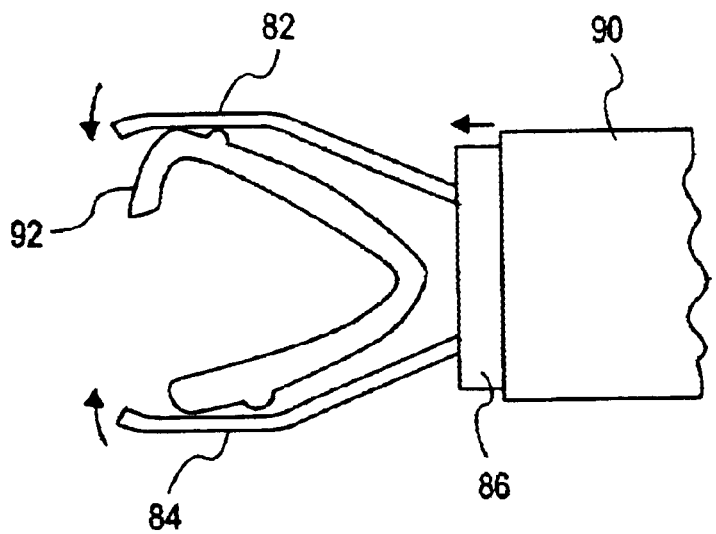
FIGS. 7A–7C show varying positions of a clip applier in accordance with the teachings of the present invention.
Figure 7B:
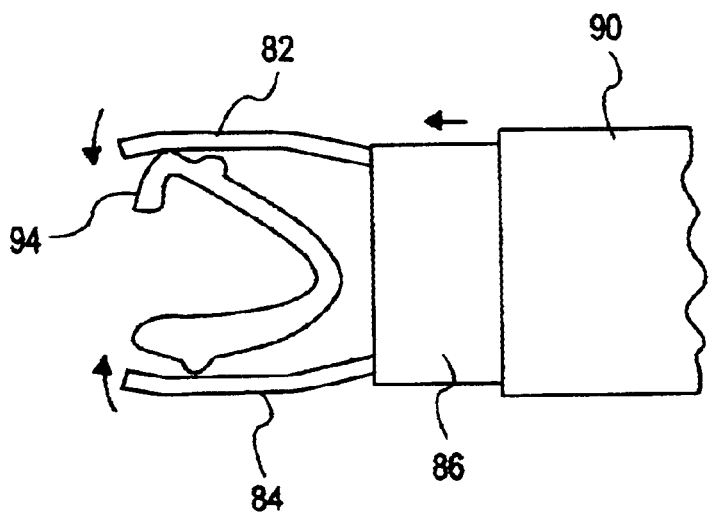
Figure 7C:
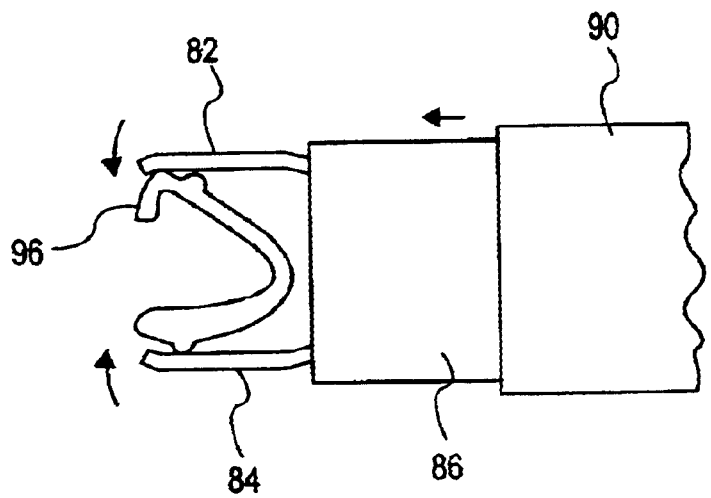

FIGS. 7A–7C show varying positions of the clip applier of FIGS. 5A and 5B engaging ligating clips of different sizes. FIG. 7A shows the clip applier in a substantially open position. When resilient sections 82 and 84 are in their natural positions, the space between sections 82 and 84 is large enough to accommodate larger ligating clips such as ligating clip 92. Once ligating clip 92 is fitted between sections 82 and 84, sections 82 and 84 can be urged (i.e., pushed) closer together by moving actuating housing 86 toward ligating clip 92 to grip ligating clip 92 more securely.

FIG. 7B shows the clip applier in a slightly closed position. As actuating housing 86 moves out from main housing 90, actuating housing 86 contacts sections 82 and 84 and urges them concurrently to close the gap between sections 82 and 84. As sections 82 and 84 are urged closer together by actuating housing 86, a smaller ligating clip such as ligating clip 94 can be held securely by the clip applier while ligating clip 94 is positioned around the target vessel.

FIG. 7C shows the clip applier in a more pronounced closed position. Actuating housing 86 moves out from main housing 90 and concurrently urges sections 82 and 84 to further close the gap between sections 82 and 84. A ligating clip 96, which is smaller than ligating clip 94, can then be fitted securely between sections 82 and 84. Once a ligating clip is held within sections 82 and 84 and positioned around the target vessel, actuating housing 86 is moved in the direction indicated in FIGS. 7A–7C until the clip is closed. It is appreciated that sections 82 and 84 can be formed with notches to provide a more secure fit for a ligating clip by mating with protrusions on the ligating clip. Sections 82 and 84 can also be textured to provide greater hold on a ligating clip. Furthermore, actuating housing 86 can have a bigger or smaller opening, depending on how much sections 82 and 84 need to be urged together in order to close the ligating clips to be used. For example, for more pronounced urging in conjunction with a smaller ligating clip, the inner diameter (assuming actuating housing 86 is in the shape of a tube) of actuating housing 86 would be smaller.

It should be noted that actuating housing 86 typically is not translatable to the point where actuating housing 86 completely hides sections 82 and 84. If actuating housing 86 is capable of moving to such a point, then actuating housing 86 could run into and possibly damage the target vessel when a ligating clip is being applied. Furthermore, sections 82 and 84 typically do not translate back and forth because such movement could damage the target vessel when a ligating clip is being applied. Thus, sections 82 and 84 are typically anchored within main housing 90 or the handle base (see FIGS. 5A and 5B) such that sections 82 and 84 do not engage in translating movement when actuating housing 86 is moving back and forth.

It is appreciated that the present invention can be used as a stand-alone device or be used in working lumens such as the VASOVIEW UNIPORT® by Origin Medsystems, Inc. of Menlo Park, Calif. Furthermore, the present invention can include an actuation limiter to lock the clip applier jaw in varying positions such that the ligating clip is not inadvertently closed or disengaged from the jaw.

In the foregoing detailed description, the apparatus and method of the present invention have been described with reference to specific exemplary embodiments. However, it will be evident that various modifications and changes may be made without departing from the broader scope and spirit of the present invention. The present specification and figures are accordingly to be regarded as illustrative rather than restrictive.

What is claimed is:

1. A surgical apparatus comprising:

a housing;

of a jaw having first and second movable sections, said jaw mateable with a plurality of ligating clips having different sizes; and an actuating mechanism disposed substantially within said housing and contacting said jaw, said jaw movable among at least a first position, a second position and a third position, at least each of said first position and said second position to accommodate a ligating clip of a different size.

2. An apparatus as in claim 1 wherein said housing is tubular.

3. An apparatus as in claim 1 wherein said actuating mechanism comprises a translatable tube disposed within said housing and surrounding said jaw, said translatable tube concurrently urging said first and second sections of said jaw when said translatable tube is translated toward a distal end of said jaw.

4. A surgical apparatus comprising:

a housing;

a jaw having first and second movable sections, said jaw mateable with a plurality of ligating clips having different sizes; and an actuating mechanism disposed substantially within said housing and contacting said jaw wherein said actuating mechanism, comprises a rod coupled to said second movable section of said jaw, said first moveable section of said jaw rotatably coupled to both said second movable section and a support member fixed to said housing.

5. A surgical apparatus comprising:

a housing;

a jaw having first and second movable sections, said jaw mateable with a plurality of ligating clips having different sizes; and an actuating mechanism disposed substantially within said housing and contacting said jaw, said jaw movable among at least a first position, a second position and a third position, at least each of said first position and said second position to accommodate a ligating clip of a different size.

wherein said actuating mechanism comprises a handle coupled to said housing, said handle and said jaw located at opposite ends of said housing.

6. A surgical apparatus comprising:

an elongated housing having a first end and a second end;

an actuating assembly having a translatable member extending through said housing and a handle coupled to said translatable member adjacent to said first end of said housing;

a fixed member coupled to said housing at said second end; and a jaw having first and second sections, said first section rotatably coupled to said fixed member and said second section, said second section coupled to said translatable member and extending away from said second end of said housing, said first section having a first range of movement and said second section having a second range of movement, said first range of movement dictated by said second range of movement, wherein said jaw being movable among at least a first position, a second position and a third position, at least each of said first position and said second position to accommodate a ligating clip of a different size.

7. An apparatus as in claim 6 wherein said first section of said jaw rotates through said first range of movement as said second section of said jaw translates through said second range of movement.

8. A surgical apparatus comprising:

an elongated outer housing having a first end and a second end;

an actuating assembly having a translatable elongated inner housing disposed within said outer housing and a handle coupled to said inner housing adjacent to said first end of said outer housing;

a jaw having a first resilient portion and a second resilient portion, said first and second resilient portions disposed within said inner housing and extending away from said second end of said outer housing;

wherein said jaw being movable among at least a first position, a second position and a third position, at least each of said first position and said second position to accommodate a ligating clip of a different size, and said inner housing concurrently urging said first and second resilient portions of said jaw when said inner housing translates through said outer housing.

9. A method comprising:

actuating a clip applier to a first position;

mating said clip applier with a first ligating clip such that said first ligating clip is held by said clip applier;

moving said clip applier adjacent to a first vessel;

applying said first ligating clip to said first vessel by actuating said clip applier to a second position wherein said clip applier to accommodate ligating clips of different sizes;

unmating said clip applier from said first ligating clip after said applying;

actuating said clip applier to a third position;

mating said clip applier with a second ligating clip such that said second ligating clip is held by said clip applier;

moving said clip applier adjacent to a second vessel; and applying said second ligating clip to said second vessel by actuating said clip applier to said second position.

10. A method as in claim 9 wherein said first and third positions are open positions and said second position is a closed position.

11. A method as in claim 9 wherein actuating said clip applier to said first position comprises sliding an actuating member toward said clip applier and wherein actuating said clip applier to said second position comprises translating said actuating member away from said clip applier.

12. A method as in claim 9 wherein said first ligating clip and said second ligating are of different size.

* * * * *